US 6,654,624 B2

(12) United States Patent
Diab et al.

(10) Patent No.: US 6,654,624 B2
(45) Date of Patent: Nov. 25, 2003

(54) PULSE OXIMETER PROBE-OFF DETECTOR

(75) Inventors: Mohamed K. Diab, Mission Viejo, CA (US); Ammar Al Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 22 days.

(21) Appl. No.: 10/027,574

(22) Filed: Dec. 19, 2001

(65) Prior Publication Data

US 2002/0072660 A1 Jun. 13, 2002

Related U.S. Application Data

(63) Continuation of application No. 09/531,820, filed on Mar. 21, 2000, now Pat. No. 6,360,114.
(60) Provisional application No. 60/126,148, filed on Mar. 25, 1999.

(51) Int. Cl.[7] ................................. A61B 5/00
(52) U.S. Cl. ...................................... 600/336
(58) Field of Search ...................... 600/336, 310, 600/322, 323, 330, 331, 481, 509, 544, 546, 547

(56) References Cited

U.S. PATENT DOCUMENTS

| | | | |
|---|---|---|---|
| 4,295,475 A | 10/1981 | Torzala | |
| 4,331,161 A | 5/1982 | Patel | |
| 4,399,824 A | 8/1983 | Davidson | |
| 4,561,440 A | 12/1985 | Kubo et al. | |
| 4,603,700 A | 8/1986 | Nichols et al. | |
| 5,226,417 A | 7/1993 | Swedlow et al. | |
| 5,368,041 A | * 11/1994 | Shambroom | 600/544 |
| 5,370,114 A | 12/1994 | Wong et al. | |
| 5,469,845 A | 11/1995 | DeLonzor et al. | |
| 5,503,148 A | 4/1996 | Pologe et al. | |
| 5,758,644 A | 6/1998 | Diab et al. | |
| 5,782,757 A | 7/1998 | Diab et al. | |
| 5,823,950 A | 10/1998 | Diab et al. | |
| 6,035,223 A | 3/2000 | Baker, Jr. | |
| 6,360,114 B1 | * 3/2002 | Diab et al. | 600/336 |

FOREIGN PATENT DOCUMENTS

| | | |
|---|---|---|
| DE | 197 28 902 A 1 | 7/1997 |
| EP | 0 182 197 A2 | 11/1985 |
| EP | 0 315 040 A1 | 10/1988 |
| GB | 2 061 496 A | 10/1980 |

* cited by examiner

Primary Examiner—Eric F. Winakur
(74) Attorney, Agent, or Firm—Knobbe, Martens, Olson & Bear, LLP

(57) ABSTRACT

An intelligent, rule-based processor provides signal quality based limits to the signal strength operating region of a pulse oximeter. These limits are superimposed on the typical gain dependent signal strength limits. If a sensor signal appears physiologically generated, the pulse oximeter is allowed to operate with minimal signal strength, maximizing low perfusion performance. If a sensor signal is potentially due to a signal induced by a dislodged sensor, signal strength requirements are raised. Thus, signal quality limitations enhance probe off detection without significantly impacting low perfusion performance. One signal quality measure used is pulse rate density, which defines the percentage of time physiologically acceptable pulses are occurring. If the detected signal contains a significant percentage of unacceptable pulses, the minimum required signal strength is raised proportionately. Another signal quality measure used in conjunction with pulse rate density is energy ratio, computed as the percentage of total energy contained in the pulse rate fundamental and associated harmonics.

33 Claims, 7 Drawing Sheets

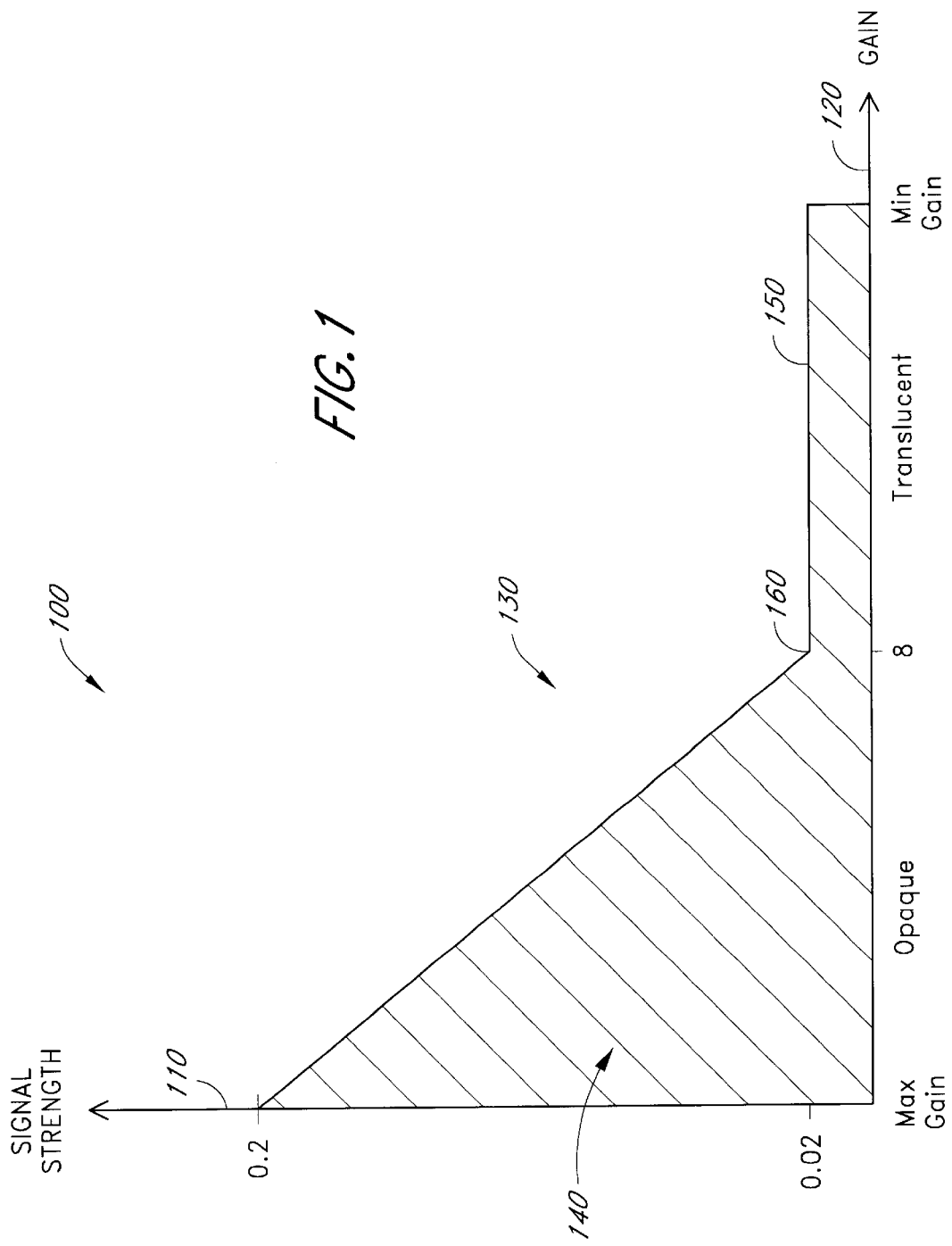

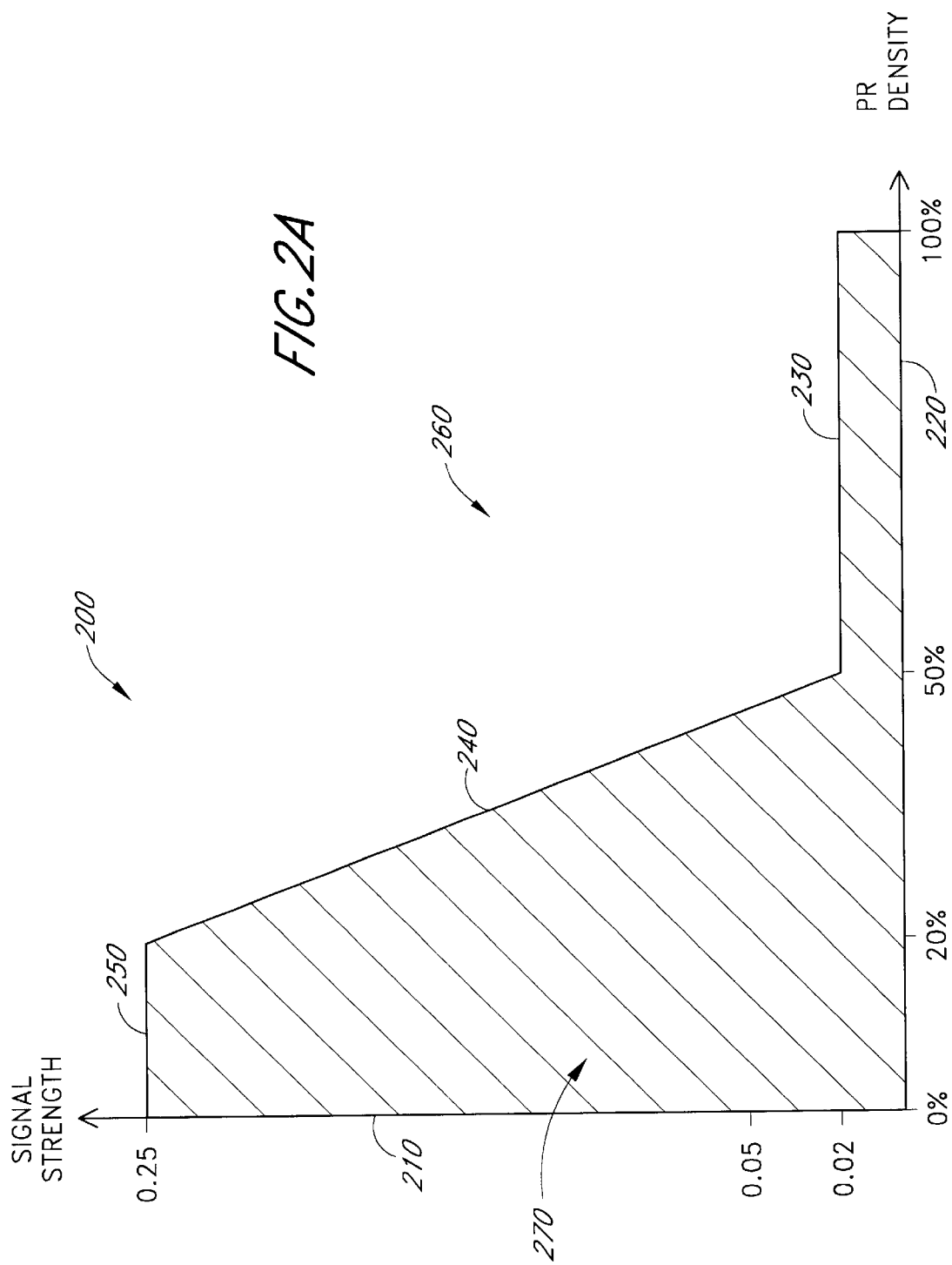

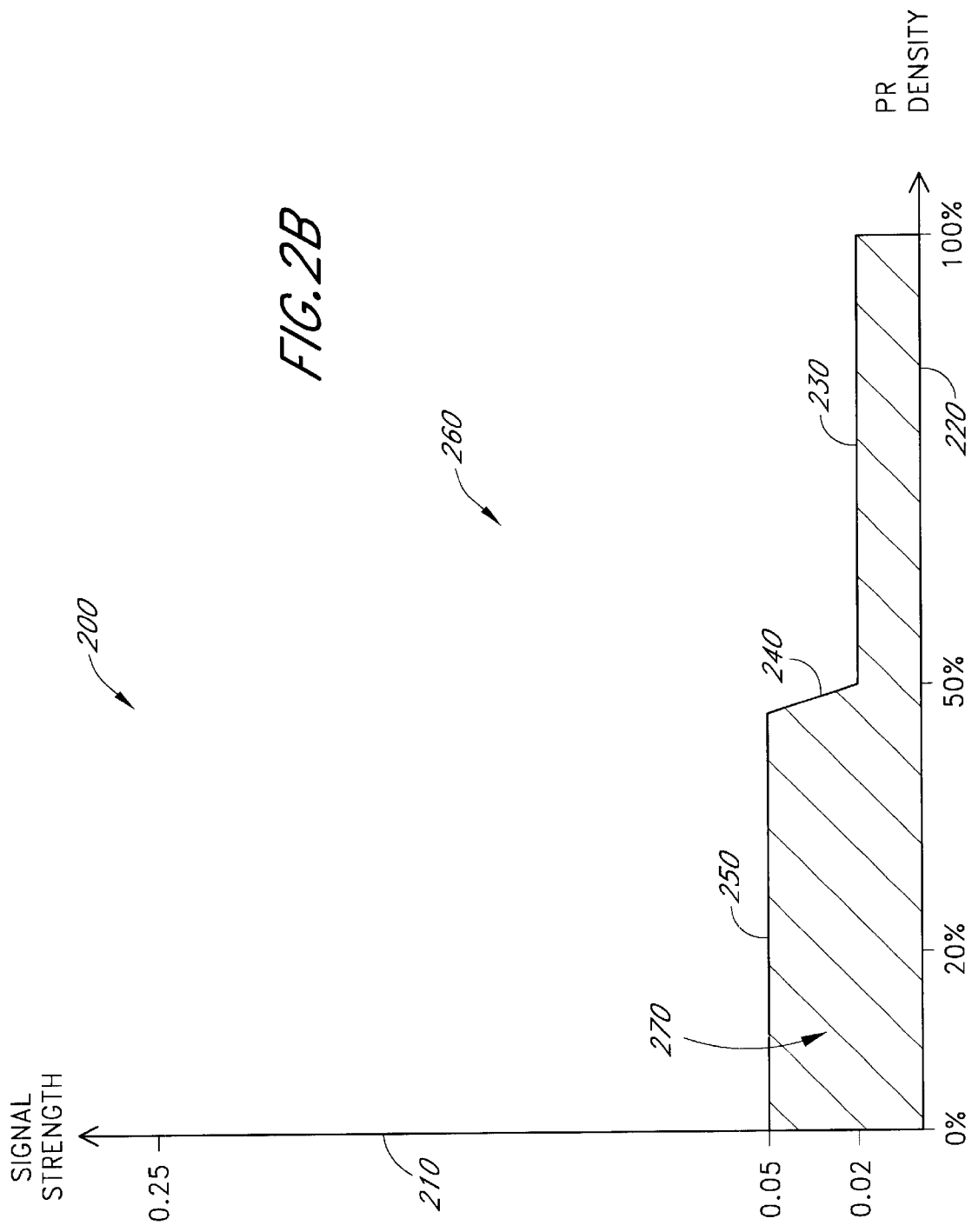

PULSE OXIMETER PROBE-OFF DETECTOR

REFERENCE TO RELATED APPLICATION

The present application is a continuation of U.S. patent application Ser. No. 09/531,820, filed Mar. 21, 2000, now U.S. Pat. No. 6,360,114, entitled "PULSE OXIMETER PROBE-OFF DETECTOR," (the parent application) and claims priority benefit under 35 U.S.C. §120 to the same. The parent application claimed a priority benefit under 35 U.S.C. §119(e) from U.S. Provisional Application No. 60/126,148, filed Mar. 25, 1999, entitled "PULSE OXIMETER PROBE-OFF DETECTOR." The present application incorporates each of the foregoing disclosures herein by reference.

BACKGROUND OF THE INVENTION

DESCRIPTION OF THE RELATED ART

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximetry system consists of a sensor attached to a patient, a monitor, and a cable connecting the sensor and monitor. Conventionally, a pulse oximetry sensor has both red and infrared (IR) light-emitting diode (LED) emitters and a photodiode detector. The sensor is typically attached to a patient's finger or toe, or a very young patient's foot. For a finger, the sensor is configured so that the emitters project light through the fingernail and into the blood vessels and capillaries underneath. The photodiode is positioned at the fingertip opposite the fingernail so as to detect the LED transmitted light as it emerges from the finger tissues.

The pulse oximetry monitor (pulse oximeter) determines oxygen saturation by computing the differential absorption by arterial blood of the two wavelengths emitted by the sensor. The pulse oximeter alternately activates the sensor LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the sensor, processing the sensor signals and displaying the patient's oxygen saturation and pulse rate. A pulse oximeter is described in U.S. Pat. No. 5,632,272 assigned to the assignee of the present invention.

SUMMARY OF THE INVENTION

To compute peripheral arterial oxygen saturation, denoted $SP_aO_2$, pulse oximetry relies on the differential light absorption of oxygenated hemoglobin, $HbO_2$, and deoxygenated hemoglobin, Hb, to compute their respective concentrations in the arterial blood. This differential absorption is measured at the red and infrared wavelengths of the sensor. In addition, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. This tissue site might also comprise skin, muscle, bone, venous blood, fat, pigment, etc., each of which absorbs light. It is assumed that the background absorption due to these surrounding tissues is invariant and can be ignored. Accordingly, blood oxygen saturation measurements are based upon a ratio of the time-varying or AC portion of the detected red and infrared signals with respect to the time-invariant or DC portion. This AC/DC ratio normalizes the signals and accounts for variations in light pathlengths through the measured tissue.

FIG. 1 illustrates the typical operating characteristics of a pulse oximeter. During a calibration phase, the pulse oximeter input gain is adjusted higher to accommodate opaque skin and lower to accommodate translucent skin at the sensor site. Variations in blood perfusion at the sensor site result in variations in input signal strength. The graph 100 shows acceptable input sensitivity as a function of gain. The y-axis 110 represents the signal strength (SS), which is the ratio of the peak-to-peak AC signal to the DC signal, expressed as a percentage. The x-axis 120 represents the gain, which is shown with decreasing values along the x-axis. The graph 100 has an unshaded region 130 representing the acceptable operating range of the pulse oximeter and a shaded region 140 representing conditions outside that operating range, which, when detected, will result in a pulse oximeter "probe off" alarm. The operating region 130 has a floor 150 at relatively low gains, representing the highest sensitivity to patients with low perfusion. Because input noise increases with gain, the operating region also has a corner point 160 below which input sensitivity is noise limited and falls off with increasing gain, i.e. increasing opacity.

A pulse oximeter with the operating characteristics shown in FIG. 1 may fail to detect a probe off condition. This problem occurs when the sensor becomes partially or completely dislodged from the patient, but continues to detect an AC signal within the operating region of the pulse oximeter. Probe off errors are serious because the pulse oximeter may display a normal saturation when, in fact, the probe is not properly attached to the patient, potentially leading to missed desaturation events.

Failure to detect a probe off condition is the result of the sensor detector receiving light directly from the emitters without transmission through the patient's tissue. The pulse oximeter is particularly vulnerable to probe off errors when operating at its highest sensitivity, where even small induced variations in light directly detected from the emitters have sufficient signal strength to be processed as a physiological signal. In a probe off condition, a detector AC signal can be induced by slight changes in the direct light path between the emitters and detector. For example, small amounts of patient motion, such as chest movement from breathing, can induce a probe off AC signal. As another example, "creep" in the sensor configuration, such as a folded sensor gradually returning to its original unfolded shape after becoming dislodged can also induce a probe off AC signal. Further restricting the operating region 130 shown in FIG. 1 can reduce probe off errors. Such restrictions, however, would also severely limit the ability of the pulse oximeter to make saturation measurements on patients with poor perfusion.

The present invention is a monitor-based improvement to detecting the probe off condition described above. Of-course, other methods of detecting the probe-off condition could be combined with the present improvement. In particular, an intelligent, rule-based processor uses signal quality measurements to limit the operating region of the pulse oximeter without significant negative impact on low perfusion performance. These signal-quality operating limits are superimposed on those of FIG. 1 to improve probe off detection. In this manner, the pulse oximeter can reject AC signals that have sufficient signal strength to fall within the operating region 130 of FIG. 1, but that are unlikely to be a plethysmograph signal. One signal quality measurement that is used is pulse rate density, which is the percentage of time detected pulses satisfy a physiologically acceptable model. Another signal quality measurement is energy ratio, which is the percentage of signal energy that occurs at the pulse rate and its harmonics. The operating region of the pulse oximeter is then defined in terms of signal strength versus gain, signal strength versus PR density and energy ratio versus predefined energy ratio limits.

In one aspect of the present invention, a probe-off detector has a signal input, a signal quality input and a probe off output. The signal quality input is dependent on a comparison between a sensor output and a physiological signal model. The probe off output provides an indication that the sensor may not be properly attached to a tissue site. The detector comprises a signal strength calculator, a stored relationship between signal strength and signal quality and a comparator. The signal strength calculator has an input in communications with the sensor signal and provides a signal strength output that is dependent on the time-varying component of the sensor signal. The stored relationship defines an acceptable operating region for the sensor. The comparator has signal strength and signal quality as inputs and provides the probe off output based on a comparison of the signal strength and the signal quality with the stored relationship.

In another aspect of the present invention, a pulse oximetry sensor signal is processed to determine if it is properly attached to a tissue site. The process steps involve setting a signal strength limit that is dependent on signal quality, calculating a signal strength value from the sensor signal, calculating a signal quality value from the sensor signal and indicating a probe off condition if the signal strength is below the limit for the signal quality value previously determined.

BRIEF DESCRIPTION OF THE DRAWINGS

FIG. 1 is a graph illustrating minimum signal strength operating limits for a pulse oximeter;

FIGS. 2A and 2B are graphs illustrating additional minimum signal strength operating limits for a pulse oximeter, based on signal quality according to the present invention;

FIG. 2A is a graph of signal quality operating limits for a pulse oximeter in normal input sensitivity mode;

FIG. 2B is a graph of signal quality operating limits for a pulse oximeter in high input sensitivity mode;

DETAILED DESCRIPTION OF THE PREFERRED EMBODIMENT

Figure 3:
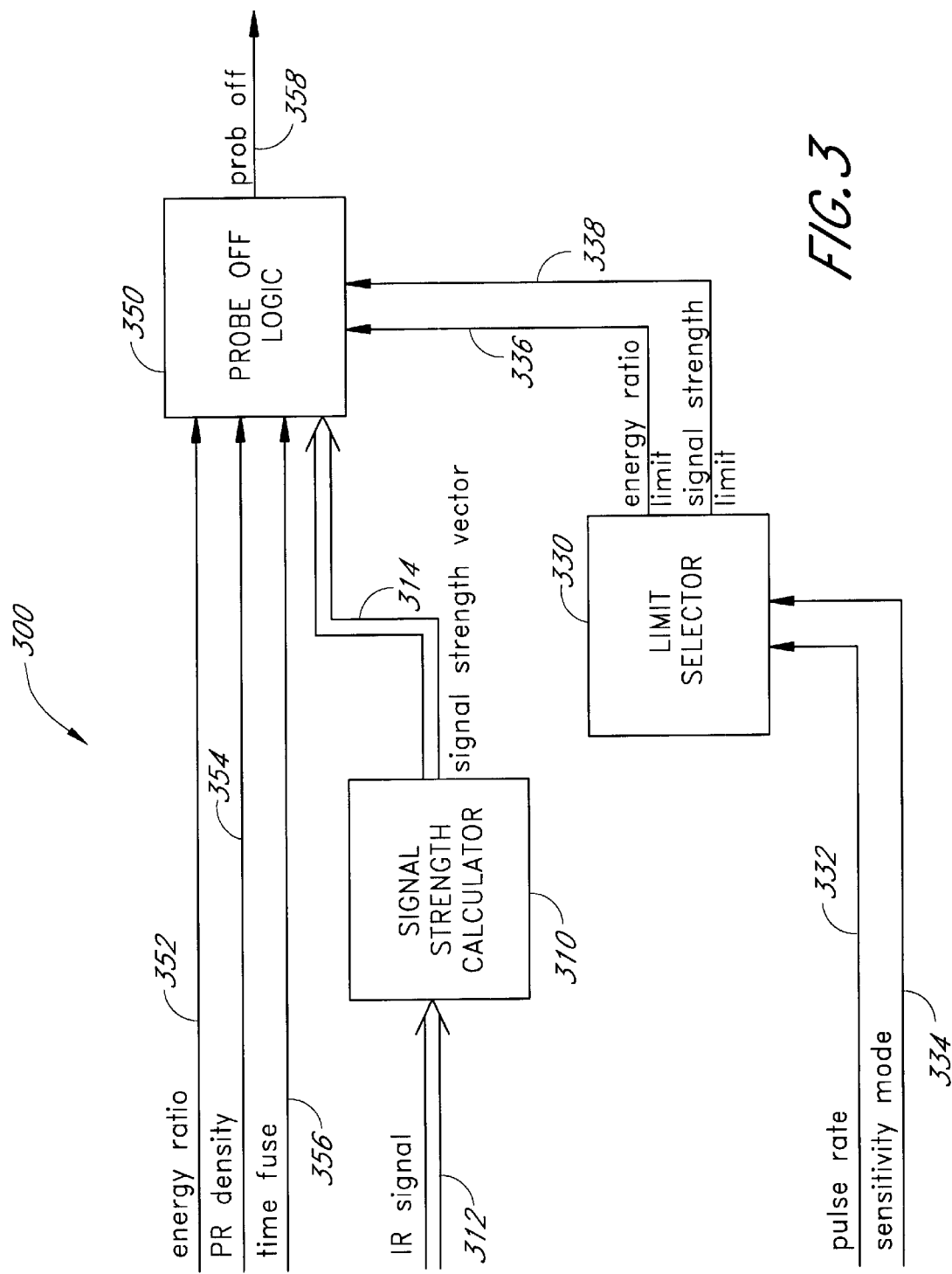
FIG. 3 is a top-level block diagram of a rule-based intelligent processor that provides the signal quality operating limits illustrated in FIGS. 2A–2B.

FIGS. 2A and 2B illustrate how the operating range of a pulse oximeter is modified based on pulse rate density according to one embodiment of the present invention. Calculation of PR density is disclosed in U.S. Provisional Patent Application No. 60/114,127 filed Dec. 30, 1998, and in U.S. patent application Ser. No. 09/471,510, filed Dec. 23, 1999, entitled "Plethysmograph Pulse Recognition Processor," which is assigned to the assignee of the current application and incorporated by reference herein. The processor described therein has a candidate pulse portion that determines a plurality of potential pulses within the input IR waveform. A physiological model portion of the processor then determines the physiologically acceptable ones of these potential pulses. The processor provides statistics regarding the acceptable pulses. One statistic is pulse density, which is the ratio of the period of acceptable pulses to the duration of a block or "snapshot" of the IR input waveform.

FIG. 2A shows a graph 200 of signal strength on the y-axis 210 versus PR density on the x-axis 220 for normal sensitivity. The operating region 260 is shown unshaded, and the probe off region 270 is shown shaded. A signal strength floor 230 of 0.02, below which a probe off condition exists for all values of PR density, determines one portion of the operating region 260. That is, no matter how many of the detected plethysmograph pulses are deemed physiologically acceptable, if the signal strength is less than 0.02, then the pulse oximeter indicates a probe off condition. A signal strength ceiling 250 of 0.25, above which the pulse oximeter is in a valid operating region for all values of PR density, determines another portion of the operating region 260. That is, signal quality is ignored if signal strength is above 0.25. Between the signal strength ceiling 250 and floor 230, acceptable signal strength is dependent on PR density. The slope of the boundary 240 defining this relationship is:

$$\text{slope} = -(0.25-0.02)/(0.5-0.2) = -0.23/0.3 = -0.7667 \quad (1)$$

Thus, this boundry can be defined by the following equivalent equations:

$$ss = -0.7667 \cdot \text{PR density} + 0.4033 \quad (2)$$

$$\text{PR density} = -1.3043 \cdot SS + 0.5261 \quad (3)$$

FIG. 2B shows a graph 200 of signal strength on the y-axis 210 versus PR density on the x-axis 220 for high sensitivity. This graph is equivalent to that of FIG. 2A except that the signal strength ceiling 250 is set at 0.05. Thus, signal quality indicated by PR density is ignored as long as the signal strength is above 0.5.

Another signal quality measure, energy ratio, is also imposed on the operating region as an absolute limit. Energy ratio is the percentage of IR signal energy occurring at the pulse rate and associated harmonics compared to total IR energy. The energy ratio is computed by transforming each block of the IR signal into the frequency domain as is well known in the art. The energy ratio is computed by identifying each peak in the resulting spectrum. In one embodiment, the peaks occurring at the pulse rate and its harmonics are identified and summed. This value is divided by the sum of the magnitudes of all peaks and output as the energy ratio. Note that energy ratio computed in this manner is not a true energy calculation because the calculations are based on the peak magnitudes and not the squared magnitudes of the IR signal. In this embodiment, the minimum energy ratio must be 0.6 if the pulse rate is greater than or equal to 30 and 0.5 otherwise. That is, 60% (or 50% for low pulse rates) of the signal must be at the pulse rate frequency or its harmonics or the pulse oximeter will indicate a probe off condition. A method for calculating the pulse rate used in this calculation is disclosed in U.S. Pat. No. 6,002,952, filed Apr. 14, 1997, entitled "Improved Signal Processing Apparatus and Method," which is assigned to the assignee of the current application and incorporated by reference herein.

FIG. 3 is a block diagram illustrating one embodiment of the improved probe-off detector 300 according to the present invention. The detector has a signal strength calculator 310, a limit selector 330 and probe-off logic 350. The signal strength calculator 310 has an IR signal 312 input. This signal is the detected sensor signal after demultiplexing, amplification, filtering and digitization. In a particular embodiment, the IR signal is input to the signal strength calculator 310 at a 62.5 Hz sample rate and in overlapping "snapshots" or blocks of 390 samples, each offset from the previous block by 25 samples. The signal strength calculator 310 creates a signal strength vector output 314 consisting of a set of signal strength scalars for each of these input blocks, as described with respect to FIG. 4 below.

The limit selector 330 has pulse rate 332 and sensitivity mode 334 inputs. When the sensitivity mode input 334 has a value of 1, it indicates that the pulse oximeter is in a normal sensitivity mode, corresponding to FIG. 2A. A value of 0 indicates the pulse oximeter is in a high sensitivity mode, corresponding to FIG. 2B. The pulse oximeter operator selects the sensitivity mode. The limit selector 330 also has energy ratio limit 336 and signal strength limit 338 outputs, which are input to the probe off logic 350 as absolute minimums of energy ratio and signal strength below which a probe off condition may be indicated 350. The relationship between the pulse rate 332 and sensitivity mode 334 inputs and the energy ratio limit 336 and signal strength limit 338 outputs is specified below:

The probe off logic 350 has as inputs energy ratio 352, PR density 334 and signal strength vector 314. These inputs are compared to the energy ratio limit 336 and signal strength limit 338 outputs from the limit selector 330 to determine the operating region of the pulse oximeter. The probe off logic 350 also has a time fuse input 356. The time fuse 356 is a counter that indicates the number of IR waveform blocks containing no acceptable pulses. Acceptable pulses are determined as described for the calculation of PR density 354, above. The time fuse 356 input is −1 if there have been no acceptable pulses in a block since startup. The time fuse 356 is reset to 0 each time no acceptable pulses are detected for an input block. For each block where there are no acceptable pulses, the time fuse 356 is incremented by one. The time fuse enables the energy ratio limit and that portion of the signal strength limits above the floor 230 (FIGS. 2A–2B). This reduces the probability of probe off alarms for transient events. In a particular embodiment, the time fuse 356 is compared to the constants −1 and 5. That is, the energy ratio and signal strength limits are enabled if there have been no acceptable pulses since startup or for more than the previous 5 IR signal blocks.

The probe off logic 350 has a Boolean probe off output 358 that is set to 1 when the probe off logic 350 detects the pulse oximeter is operating outside permissible limits. Otherwise, the probe off output 358 is 0. The probe off output can be used by the pulse oximeter to trigger a probe off alarm and error message to alert medical personnel to inspect and reattach the sensor or take other appropriate action. The probe off logic 350 is described in more detail below with respect to FIG. 5.

Figure 4:
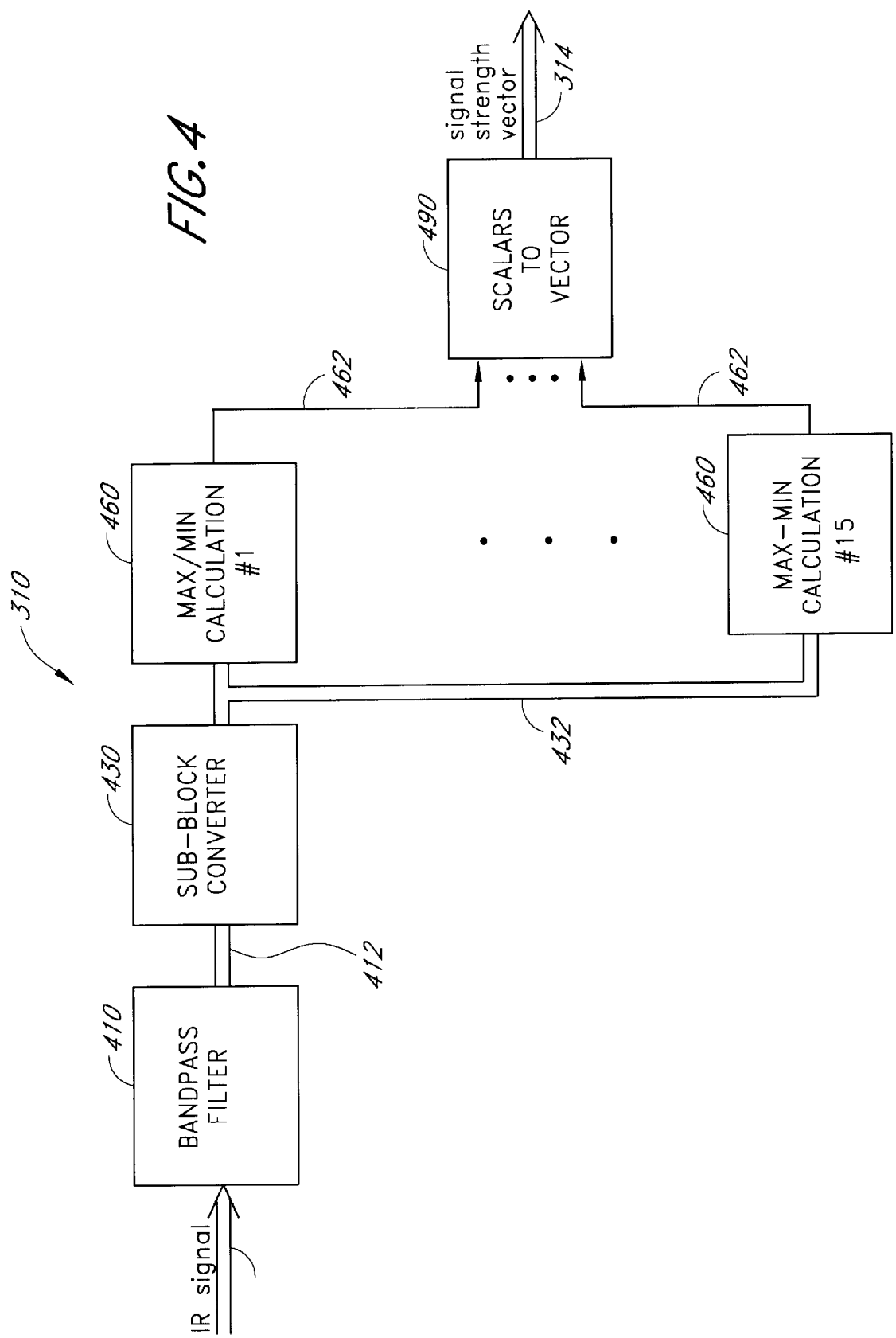
FIG. 4 is a detailed block diagram of the signal strength calculator portion of FIG. 3.

FIG. 4 shows further details of the signal strength calculator 310 (FIG. 3). Each 390 sample block of the IR signal 312 is initially filtered 410 to remove any trends in the IR signal 312 that could cause an error in the signal strength calculations. In a particular embodiment, the filter 410 is a bandpass FIR filter with cutoff frequencies of 50 Hz and 550 Hz and a 151 tap Kaiser window having a shape parameter of 3.906. As a result, 150 samples are lost from each 390 sample input block. Thus, the filtered IR output 412 consists of 240 sample blocks.

Each 240 sample block of the filtered IR output 412 is converted 430 into multiple overlapping sub-blocks. In a particular embodiment, the sub-blocks each consist of 100 samples, and each sub-block is offset by 10 samples from the previous sub-block. Thus, the sub-block converter 430 creates 15 sub-block outputs 432 for each 240 sample filtered IR block 412. For each sub-block, a max-min calculation 460 is performed. That is, the minimum sample magnitude in a particular sub-block is subtracted from the maximum sample magnitude in that sub-block. Each max-min output 462 is a single scalar representing the signal strength of a particular sub-block. A scalar-to-vector conversion 490 combines the max-min outputs 462 into a vector output 314 containing multiple signal strength values representing the signal strength of a particular block of the IR signal 312.

Figure 5:
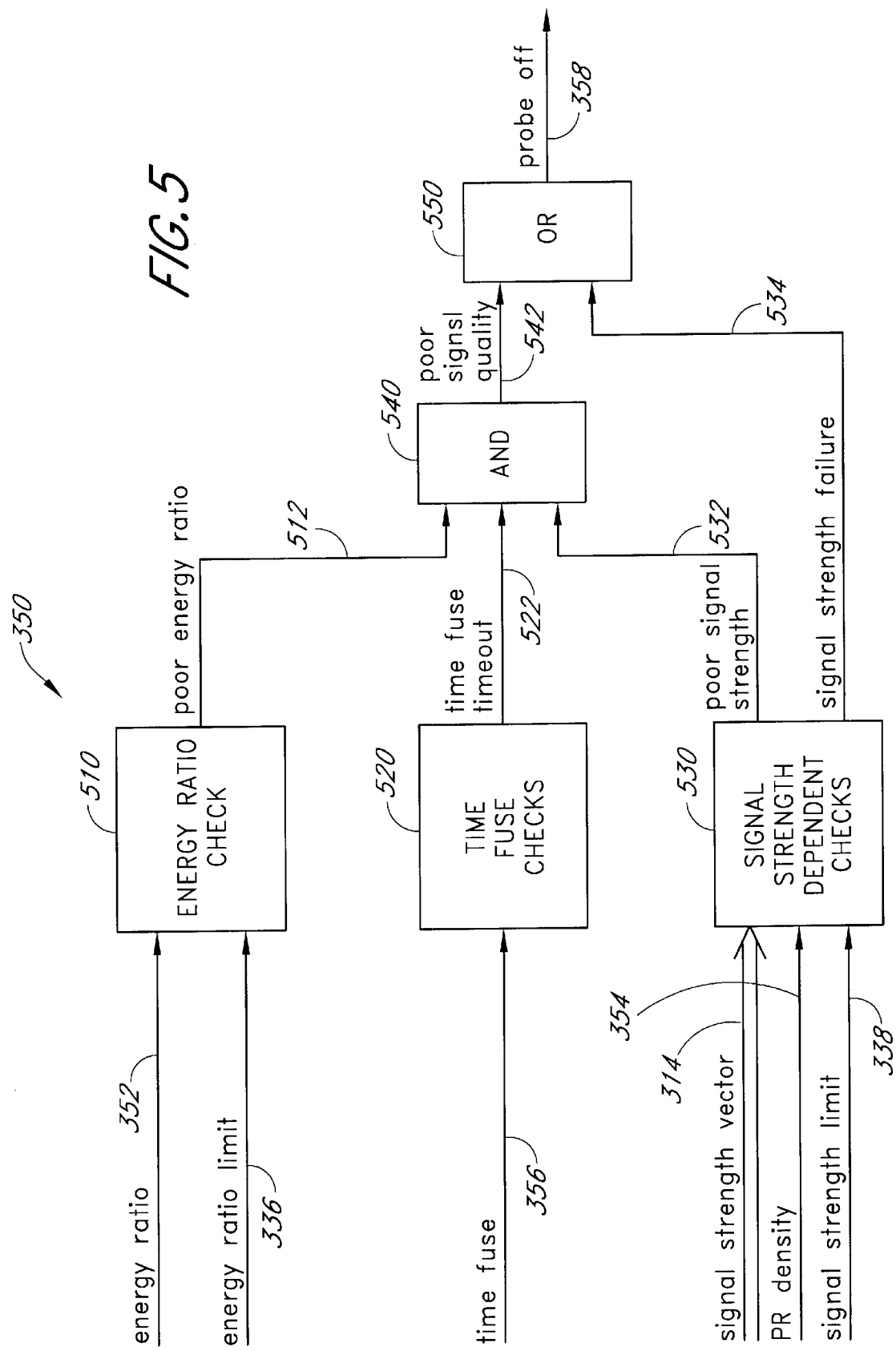
FIG. 5 is a detailed block diagram of the probe off logic portion of FIG. 3.

FIG. 5 provides further detail of the probe off logic 350 (FIG. 3). The probe off logic 350 has three functional checks that each provide a Boolean output. An energy ratio check 510 compares the energy ratio 352 against the energy ratio limit 336 provided by the limit selector 330 (FIG. 3), specified in the table above. The energy ratio check 510 sets the "poor energy ratio" output 512 if the energy ratio 352 is below the energy ratio limit 336.

A time fuse check 520 determines if the time fuse 356 indicates no acceptable pulses have occurred in the IR signal 312 (FIG. 3) for a sufficiently long time period. If so, a timeout output 522 is set. In a particular embodiment, the time fuse check 520 consists of comparators that determine if the time fuse 356 is −1 or greater than 5, indicating no acceptable pulses since startup or for a longer period than the past 5 blocks of IR signal 312.

The signal strength dependent checks 530 determine if the pulse oximeter is within the operating limits described above with respect to FIGS. 2A and 2B. If the signal strength, as determined by the signal strength vector 314, is below the floor 230 (FIGS. 2A–B), then the signal strength failure output 534 is set. If the signal strength is above the floor 230 (FIGS. 2A–B) but otherwise outside the operating region, i.e. within the shaded region 270 (FIGS. 2A–B) above the floor 230 (FIGS. 2A–2B), then the "poor signal strength" output 532 is set.

A logical AND function 540 sets a "poor signal quality" output 542 if the poor energy ratio 512, poor signal strength 532 and timeout 522 outputs are set. A logical OR function 550 sets the probe off output 358 if the poor signal quality 542 or the signal strength failure 534 outputs are set.

Figure 6:
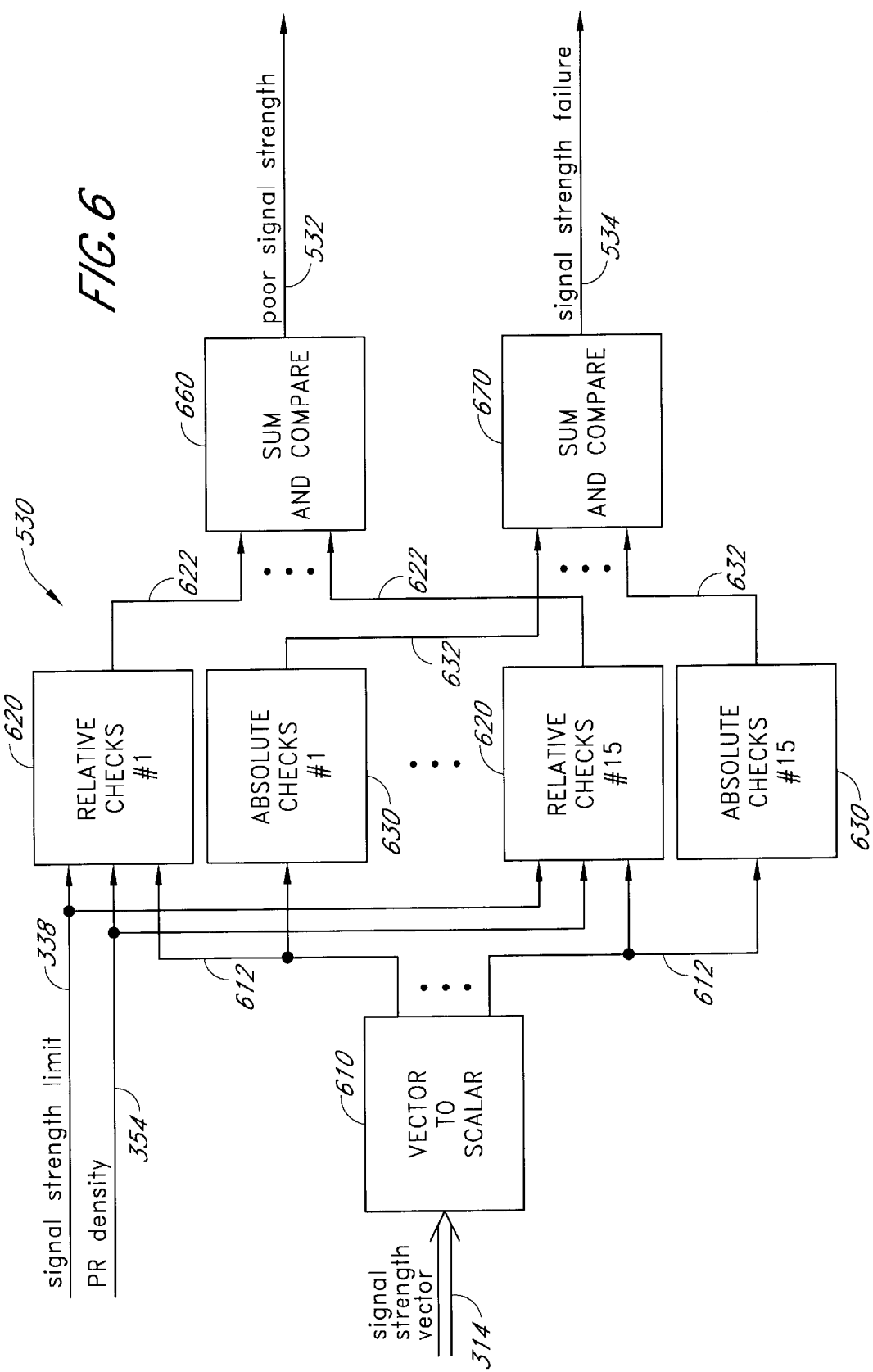
FIG. 6 is a detailed block diagram of the signal strength dependent checks portion of FIG. 5.

FIG. 6 shows a particular embodiment of the signal strength dependent checks 530 (FIG. 5). The signal strength vector 314 is converted 610 into the 15 individual signal strength scalars 612. Relative checks 620 and absolute checks 630 are performed on each of the 15 scalars 612. Each relative check 620 determines if signal strength is within the signal strength limit 338 relative to PR density 354. That is, each relative check output 622 is set according to the following, see Eq. 3 above:

| INPUT STATE | RESULT |
| --- | --- |
| SS ≥ SS limit | output = 0 |
| PR density > −1.3043 · SS + 0.5261 | output = 0 |
| (SS < SS limit) AND | output = 1 |
| PR density < −1.3043 · SS + 0.5261 | |

Each absolute check 630 determines if the signal strength is above the absolute minimum floor 230 (FIGS. 2A–2B).

That is, each absolute check output 632 is set according to the following:

| INPUT STATE | RESULT |
|---|---|
| SS ≥ 0.02 | output = 0 |
| SS < 0.02 | output = 1 |

The 15 relative check outputs 622 are processed by a sum and compare 660, which performs an arithmetic sum of these outputs 622. If the sum is equal or greater than 5, the poor signal strength output 532 is set. That is, poor signal strength is indicated if at least ⅓ of the scalars in the signal strength vector 314 fail their relative checks 620. Likewise, the 15 absolute check outputs 632 are processed by a sum and compare 670, which performs an arithmetic sum of these outputs 632. If the sum is equal or greater than 5, the signal strength failure output 534 is set. That is, a signal strength failure is indicated if at least ⅓ of the scalars in the signal strength vector 314 fail the absolute checks 630.

This improvement to detecting pulse oximetry probe off conditions has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A detector for determining when a physiological sensor may not be properly positioned with respect to a measurement site, the detector comprising:
    a signal strength calculator which processes an input signal expected to be representative of at least one parameter measured by a physiological sensor to produce an output representative of a strength of the input signal; and
    logic which indicates that the input signal may not represent the parameter when a predetermined portion of the output is below a threshold value, wherein the threshold value comprises a floor value below which a probe-off condition exists for all values of the output, and wherein the floor value comprises a ratio of a first value of a substantially alternating part of the output to a second value of a substantially non-alternating part of the output.

2. The detector of claim 1, wherein the ratio comprises about 0.02.

3. The detector of claim 1, wherein the output comprises a group of samples, and wherein the predetermined portion of the output comprises about one-third of the group.

4. The detector of claim 3, wherein the group of samples comprises a group of ratios, each ratio comprising a first value of a substantially alternating part of the output to a second value of a substantially non-alternating part of the output.

5. A detector for determining when a physiological sensor may not be properly positioned with respect to a measurement site, the detector comprising:
    a signal strength calculator which processes an input signal expected to be representative of at least one parameter measured by a physiological sensor, to produce an output representative of a signal strength of the input signal; and
    logic which indicates that a probe-off condition may exist when both a predetermined portion of the output is below a signal strength threshold and a signal quality of the input signal falls within a non-operative region.

6. The detector of claim 5, wherein the signal strength threshold is dependent upon a sensitivity mode of the physiological sensor.

7. The detector of claim 6, wherein the sensitivity mode is set by an operator.

8. The detector of claim 5, wherein the signal strength threshold comprises a ratio of a first value of a substantially alternating part of the output to a second value of a substantially non-alternating part of the output.

9. The detector of claim 8, wherein the ratio comprises a value above which a probe-off condition does not exist for all values of the output.

10. The detector of claim 8, wherein the ratio comprises a value of about 0.25.

11. The detector of claim 8, wherein the ratio comprises a value of about 0.05.

12. The detector of claim 5, wherein the signal quality comprises a comparison of the input signal with one or more physiological signal models.

13. The detector of claim 5, wherein the non operative-region comprises a region defined by a relationship between the output signal and the signal quality.

14. The detector of claim 5, further comprising a stored timeout value representative of whether the predetermined portion of the output is valid.

15. The detector of claim 5, wherein the logic indicates that the probe-off condition may exist when all of the stored timeout value indicates the output is valid, and when both the predetermined portion of the output is below the signal strength threshold and the signal quality of the input signal falls within the non-operative region.

16. The detector of claim 5, further comprising a stored energy ratio representative of whether a measurement of energy in the input signal is above threshold value.

17. The detector of claim 16, wherein the logic indicates that a probe-off condition may exist when all of the stored energy ratio is above the threshold value, and when both the predetermined portion of the output is below the signal strength threshold and the signal quality of the input signal falls within the non-operative region.

18. The detector of claim 16, wherein the logic indicates that a probe-off condition may exist when all of the stored energy ratio is above the threshold value, a timeout value indicates the output includes valid data, and when both the predetermined portion of the output is below the signal strength threshold and the signal quality of the input signal falls within the non-operative region.

19. A detector for determining when a physiological sensor may not be properly positioned with respect to a measurement site, the detector comprising:
    a limit selector outputting an energy ratio limit dependent upon a sensitivity mode of a physiological sensor; and
    logic which indicates that a probe-off condition may exist when an energy ratio representative of an amount of energy in an input signal expected to be representative of at least one parameter measured by a physiological sensor, is below the energy ratio limit.

20. The detector of claim 19, wherein the energy ratio comprises a ratio of signal energy in the input signal at a detected pulse rate to a total energy of the input signal.

21. The detector of claim 20, wherein the ratio of signal energy comprises the ratio of signal energy in the input signal at a detected pulse rate and at least one harmonic of the detected pulse rate.

22. The detector of claim 19, wherein the energy ratio limit is selected by an operator.

23. The detector of claim 19, wherein the energy ratio limit comprises about 0.6.

24. The detector of claim 19, wherein the energy ratio limit comprises about 0.5.

25. The detector of claim 19, wherein the logic indicates that a probe-off condition may exist when both a timeout value indicates the input signal is valid, and when the energy ratio is below the energy radio limit.

26. The detector of claim 19, wherein the logic indicates that a probe-off condition may exist when all of a timeout value indicates the input signal is valid, and when both a predetermined portion of an output signal representing the signal strength of the input signal is below a signal strength threshold and a signal quality of the input signal falls within the non-operative region.

27. A pulse-off detector for determining when a physiological sensor may not be properly positioned on a measurement site by monitoring characteristics of a signal expected to be representative of at least one parameter measured by the physiological sensor, the pulse-off detector comprising:

an energy ratio check which compares an energy ratio of a signal expected to be representative of at least one parameter measured by a physiological sensor, with an energy ratio limit;

a time fuse check which determines whether no acceptable values of the signal have been received;

a signal strength check which determines whether the physiological sensor is within operating limits defined by a relationship between a signal strength characteristic of the signal and a signal quality characteristic of the signal; and logic which indicates that the physiological sensor may be in an off-probe condition based on at least one of the energy ratio check, the time fuse check and the signal strength check.

28. The pulse-off detector of claim 27, wherein the logic indicates that the physiological sensor may be in the off-probe condition when the signal strength check indicates that the signal strength characteristic is below a signal strength threshold.

29. The pulse-off detector of claim 28, wherein signal strength threshold comprises a value below which an off-probe condition exists for all values of the signal.

30. The pulse-off detector of claim 27, wherein the logic indicates that the physiological sensor may be in the off-probe condition when the signal strength check indicates that the signal strength characteristic is outside the operating limits.

31. The pulse-off detector of claim 27, wherein the logic indicates that the physiological sensor may be in the off-probe condition when the energy ratio check indicates that the energy ratio is below the energy ratio limit.

32. The pulse-off detector of claim 31, wherein the energy ratio limit is set by an operator.

33. The pulse-off detector of claim 27, wherein the logic indicates that the physiological sensor may be in the off-probe condition during a first signal condition or a second signal condition, wherein the first signal condition includes the signal strength check indicating that the signal strength characteristic is below a signal strength threshold, and wherein the second signal condition includes all of (a) the signal strength check indicating that the signal strength characteristic is outside the operating limits, (b) the energy ratio check indicating that the energy ratio of the signal is below the energy ratio limit, and (c) the time fuse check determining that no acceptable values of the signal have been received.

* * * * *

UNITED STATES PATENT AND TRADEMARK OFFICE
CERTIFICATE OF CORRECTION

| | | |
|---|---|---|
| PATENT NO. | : 6,654,624 B2 | Page 1 of 1 |
| APPLICATION NO. | : 10/027574 | |
| DATED | : November 25, 2003 | |
| INVENTOR(S) | : Mohamed K. Diab et al. | |

It is certified that error appears in the above-identified patent and that said Letters Patent is hereby corrected as shown below:

In Column 1, Line 1, please insert -- IMPROVED -- before "PULSE".

In Column 1, Line 1, please insert -- IMPROVED -- before "PULSE".

In Column 4, Line 32, please delete "boundry" and insert -- boundary --, therefore.

In Column 5, Line 28, below "specified below:" please insert

--  --.

In Sheet 4 of 7, FIG. 3, Line 2, above Reference Numeral 358, please delete "prob" and insert -- probe --, therefore.

In Sheet 6 of 7, FIG. 5, Line 2, above Reference Numeral 542, please delete "signsl" and insert -- signal --, therefore.

In Column 9, Line 8, Claim 25, please delete "radio limit" and insert -- ratio limit --, therefore.

Signed and Sealed this

Nineteenth Day of June, 2007

JON W. DUDAS
*Director of the United States Patent and Trademark Office*